(12) United States Patent
Dane et al.

(10) Patent No.: US 8,287,009 B2
(45) Date of Patent: Oct. 16, 2012

(54) LATCH FOR A MEDICAL INSTRUMENT STERILIZATION CONTAINER

(75) Inventors: Gary T. Dane, Bow, NH (US); Kraig Herman Allen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 105 days.

(21) Appl. No.: 12/828,813

(22) Filed: Jul. 1, 2010

(65) Prior Publication Data

US 2011/0000916 A1  Jan. 6, 2011

Related U.S. Application Data

(60) Provisional application No. 61/222,656, filed on Jul. 2, 2009.

(51) Int. Cl.
E05C 3/16 (2006.01)
E05C 19/06 (2006.01)
E05C 19/10 (2006.01)
E05C 1/02 (2006.01)
B65D 45/00 (2006.01)

(52) U.S. Cl. ............ 292/56; 292/80; 292/125; 292/179; 292/256

(58) Field of Classification Search ............ 292/56, 292/80, 87, 88, 89, 125, 107, 179, 180, 256, 292/256.63, 303, 281, DIG. 37; 312/215
See application file for complete search history.

(56) References Cited

U.S. PATENT DOCUMENTS

| | | | |
|---|---|---|---|
| 3,881,758 A * | 5/1975 | Gross | 292/87 |
| 4,046,254 A | 9/1977 | Kramer | |
| 4,270,668 A * | 6/1981 | Berfield | 220/324 |
| 4,665,596 A * | 5/1987 | Green | 24/662 |
| 4,801,165 A * | 1/1989 | Pyle | 292/249 |
| 5,281,400 A | 1/1994 | Berry | |
| 5,394,983 A * | 3/1995 | Latulippe et al. | 206/370 |
| 5,628,970 A * | 5/1997 | Basile et al. | 422/297 |
| 5,732,821 A * | 3/1998 | Stone et al. | 206/370 |
| 6,012,577 A * | 1/2000 | Lewis et al. | 206/370 |
| 6,405,863 B1 | 6/2002 | Dhindsa | |
| 6,585,942 B1 * | 7/2003 | Bussell et al. | 422/300 |
| 6,592,000 B1 * | 7/2003 | Owens et al. | 220/324 |
| 2005/0158222 A1 | 7/2005 | Battenhausen | |

FOREIGN PATENT DOCUMENTS

| | | |
|---|---|---|
| JP | 61091547 U | 6/1986 |
| JP | 02520485 Y2 | 9/1996 |
| JP | 2001343693 A | 12/2001 |
| JP | 2004231191 A | 8/2004 |
| JP | 2005225538 A | 8/2005 |

* cited by examiner

*Primary Examiner* — Thomas Beach
*Assistant Examiner* — Nathan Cumar
(74) *Attorney, Agent, or Firm* — Hayes Soloway P.C.

(57) ABSTRACT

The system contains a latch mechanism for a container having a first container portion and a second container portion comprising a guide part attached to the first container portion. A slide part is carried by the guide part, shiftable relative to the guide part between a closed position restraining the second container portion and an open position releasing the slide part from the second container portion. A guide catch part is integral with said guide part and a slide part including a depressible flap. A slide catch part is integral with said depressible flap. Interaction between said guide catch part and said slide catch part restrains said slide part against movement from said closed position into said open position. Actuating said depressible flap releases said slide catch part from being restrained by said guide catch part and frees the slide part to move from the closed to open position.

20 Claims, 4 Drawing Sheets

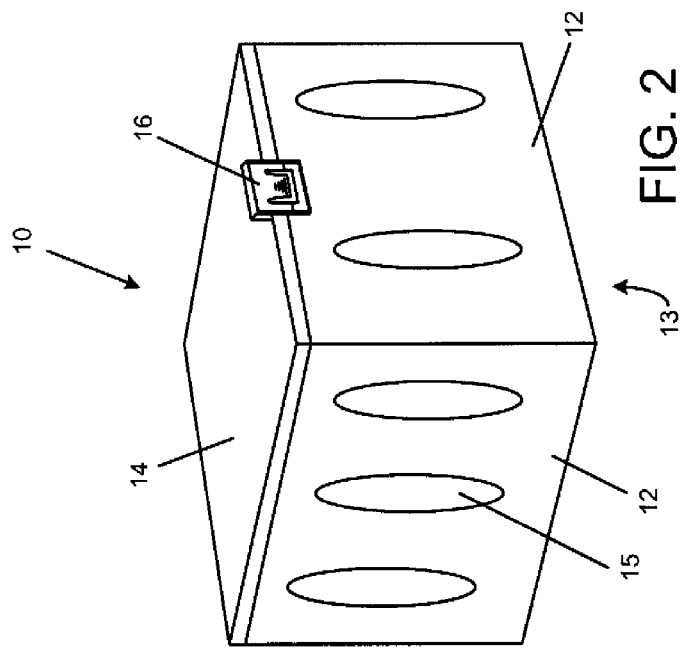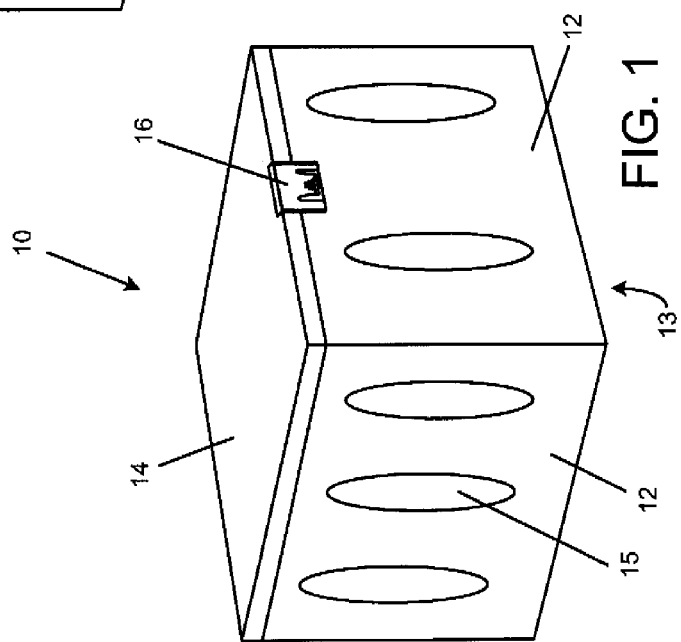

LATCH FOR A MEDICAL INSTRUMENT STERILIZATION CONTAINER

CROSS REFERENCE TO RELATED APPLICATION

This application claims benefit of U.S. Provisional Application Ser. No. 61/222,656 filed Jul. 2, 2009, the entire disclosure of which is incorporated herein by reference.

FIELD OF THE DISCLOSURE

The present disclosure is generally related to latches, and more particularly is related to latches for medical instrument sterilization containers.

BACKGROUND OF THE DISCLOSURE

This disclosure relates to a latching mechanism for the purpose of securing a lid to a container base and has specific but not limited application to a sliding latch usable with sterilization containers for such things as medical instrumentation.

Most latch mechanisms for sterilization containers and instrument containers are of metallic manufacture and generally of an over center type of operation. Some latches have sharpened edges which can cause tearing of a sterile barrier or a gloved hand and are not easily opened in medical situations where many times time is critical. In this disclosure a slide latch is provided. The latch includes a guide part which is secured to the lid of the container and an interfitting slide part which moves relative to the guide part. The slide part of the latch mechanism includes a lip which when the slide part is retracted fits over the container base serving to secure the lid to the base. The guide and slide parts of the latch mechanism are preferably formed of an injection molded plastic. The latch assembly may be of a specific color so as to identify the type of instrumentation or purpose of the container. Also, the latch mechanism can be easily and simply secured to the lid of the container by a snap fit interconnect.

Thus, a heretofore unaddressed need exists in the industry to address the aforementioned deficiencies and inadequacies.

SUMMARY OF THE DISCLOSURE

Embodiments of the present disclosure provide a system for a latch for medical instrument sterilization containers. Briefly described, in architecture, one embodiment of the system, among others, can be implemented as follows. The system contains a latch mechanism for a container having a first container portion and a second container portion, the latch mechanism having a guide part attached to the first container portion. A slide part is carried by the guide part, shiftable relative to the guide part between a closed position restraining the second container portion and an open position releasing said slide part from the second container portion. The system includes a guide catch part integral with the guide part. The slide part includes a depressible flap and a slide catch part integral with the depressible flap, wherein interaction between the guide catch part and the slide catch part restrains the slide part against movement from the closed position into the open position, whereby actuating the depressible flap releases the slide catch part from being restrained by the guide catch part and frees the slide part to move from the closed position to the open position.

The present disclosure can also be viewed as providing a method for unlatching a latch mechanism having an open and a closed position. In this regard, one embodiment of such a method, among others, can be broadly summarized by the following steps: attaching a guide part to a first container portion; actuating a depressible flap, attached to a slide part, thereby freeing a slide catch part integral with the slide part from the restraint in the closed position of a guide catch part integral with the guide part; retaining the depressible flap in an actuated position; and shifting the slide part relative to the guide part to the open position, wherein the slide part is guided by at least one sliding rail engaged with at least one guiding rail thereby disengaging at least one lip integral with the slide part from a second container portion.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is an illustration of a perspective view of a container with the latch in a closed position in accordance with a first exemplary embodiment of the present disclosure.

FIG. 2 is an illustration of a perspective view of a container with the latch in an open position in accordance with the first exemplary embodiment of the present disclosure.

DETAILED DESCRIPTION

Figure 3:
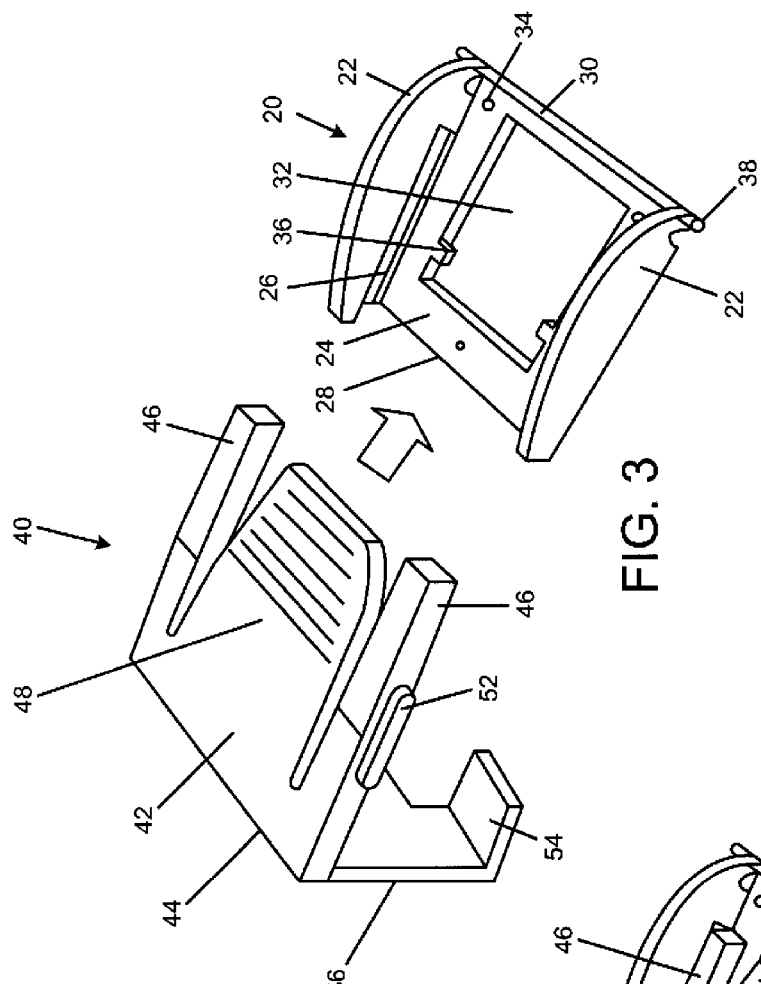
FIG. 3 is an illustration of an exploded view of the latch mechanism of FIG. 1, in accordance with the first exemplary embodiment of the present disclosure.

FIG. 1 is an illustration of a perspective view of a container 10 with the latch mechanism 16 in a closed position, in accordance with a first exemplary embodiment of the present disclosure. FIG. 2 is an illustration of a perspective view of a container 10 with the latch mechanism 16 in an open position, in accordance with the first exemplary embodiment of the present disclosure. The container 10 includes a plurality of sides 12. A lid 14 is included with the container 10. A latch mechanism 16 is included with the container 10. The latch mechanism 16 is secured to one of the plurality of sides 12 of the container 10. The latch mechanism 16 may also be secured to the lid 14. The form and style of the container 10 may vary but will generally include a plurality of sides 12, a base 13 and a lid 14 which may be of a metallic or plastic composition.

The container 10 may include one latch mechanism 16 or a plurality of latch mechanisms 16 that secure one of a side 12, lid 14 or base 13 of the container 10 to one of the other. For example, a latch mechanism 16 may be located on one of the plurality of side 12 and engage a lid 14, or located on a lid 14 and engage a side 12. If the container 10 is being utilized as a sterilization device for sterilizing medical instruments, there may be a plurality of openings 15 formed in a combination of the plurality of sides 12, the base 13 and lid 14 to allow for the escape and passage for the sterilization material, such as steam. The latch mechanism 16 is secured to one of the plurality of sides 12 of the container 10, to the lid 14 or the base 13. The latch mechanism 16 may be secured by a hinge attached to the guide part 20 and/or may be secured with a threaded fastener, like a screw. One having skill in the art will recognize that there are many known ways and structures to secure the latch mechanism 16 to the container 10. These ways and structures may include, but are not limited to a permanent attachment like bonding, an integral attachment such as molding or casting, and a removable attachment such as an intermitting clip system, all of which are considered within the scope of this disclosure.

Figure 4:
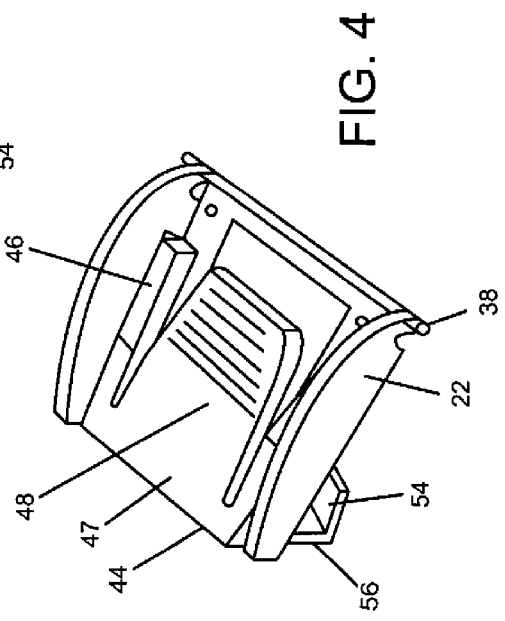
FIG. 4 is an illustration of the latch mechanism of FIG. 1, in accordance with the first exemplary embodiment of the present disclosure.

FIG. 3 is an illustration of an exploded view of the latch mechanism 16 of FIG. 1, in accordance with the first exemplary embodiment of the present disclosure. FIG. 4 is an illustration of the latch mechanism 16 of FIG. 1 in a closed position, in accordance with the first exemplary embodiment of the present disclosure. The latch mechanism 16 includes a guide part 20 and a slide part 40. The guide part 20 and the slide part 40 are situated to be interconnected, and once interconnected, the slide part 40 may be shifted in a forward and rear direction, with respect to a front end 28 and a rear end 30 of the guide part 20.

With reference to FIGS. 1 and 2, the guide part 20 is secured to a portion of the container 10, such as the lid 14 or a sidewall 12, and includes a frame 24 that extends between a pair of guide rail support structures 22. Each of the guide rail support structures 22 form in conjunction with the frame 24 a guiding rail 26, which extends from the front end 28 of the guide part to approximately the rear end 30. The design of the guide part 20 may also include a single or a plurality of guide rail support structures 22. Frame 24 of guide part 20 has an inner opening 32, which extends inwardly from the rear end 30 to the front end 28. At least one threaded fastener hole 34 may be included in the frame 24 to facilitate attachment of the guide part 20 to the container 10 with a threaded fastener. The frame 24 also includes at least one guide catch part 36 integral with the frame 24. The guide catch part 36 may also be attached to the frame 24 with any other design known to the art, including but not limited to a permanent, semi-permanent or removable attachment. The at least one guide catch part 36 may be located on opposing sides of the frame 24, extending over the inner opening 32. The at least one guide catch part 36 may extend perpendicular to the plane of the frame 24. In other words, the guide catch part 36 may be raised off the plane of the frame 24. The guide catch part 36 may be composed of a rigid material, or any other material capable of restraining the slide part 40 from moving such as plastic, metal, rubber or a synthetic substance.

Guide part 20 may be secured to any portion of the container 10 such as the lid 14 or a side 12 by gluing, bonding, ultrasonic welding or any other permanent, semi-permanent or removable attachment means. Preferably, the guide part 20 is designed to hinge to the container 10. This is accomplished by providing a hinge 38 adjacent to the rear part 30 of the frame 24. The container 10 may include a feature to receive the hinge 38.

Slide part 40 of latch mechanism 16 includes a frame 42. The frame 42 includes a frame corner 44 located at the end of one side of the frame 42. Integral with the frame 42, starting at the frame corner 44 and extending in one direction is at least one slide rail support structure 46. The first embodiment of the present disclosure includes two slide rail support structures 46 positioned at opposing sides of the frame 42, however any number of slide rail support structures 46 may be included. On the outermost face of the slide rail support structure 46 is a sliding rail 52. The sliding rail 52 is positioned to be received by the guiding rail 26 of the guide part 20. Once received by the guide part 20, the sliding rail 52 may be substantially shifted in the forward and backward directions, in respect to the front end 28 and the rear end 30 of the guide part 20.

In between the two slide rail support structures 46, integral with the frame 42, starting at the frame corner 44 and extending parallel to the slide rail support structures 46 is a depressible flap 48. The depressible flap 48 may be composed of a rigid material capable of holding its shape but able to be biased by a minimal force such as plastic, metal, rubber or a synthetic substance. The depressible flap 48 will generally be integral with the frame 42, but may also be permanently, semi-permanently or removably attached by any means known to those having skill in the art. The slide part 40 also includes a front plate 56, integral with the frame 42 of the slide part 40, and at least one lip 54 connected to the front plate 56.

Figure 6:
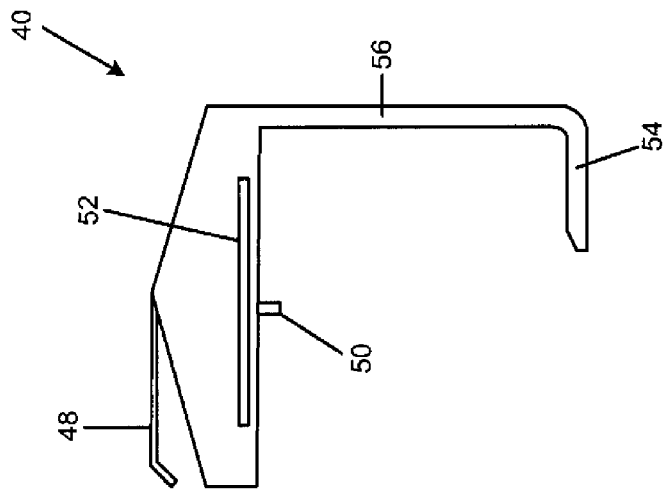
FIG. 6 is an illustration of a side view of the latch mechanism in FIG. 1, in accordance with the first exemplary embodiment of the present disclosure.
Figure 5:
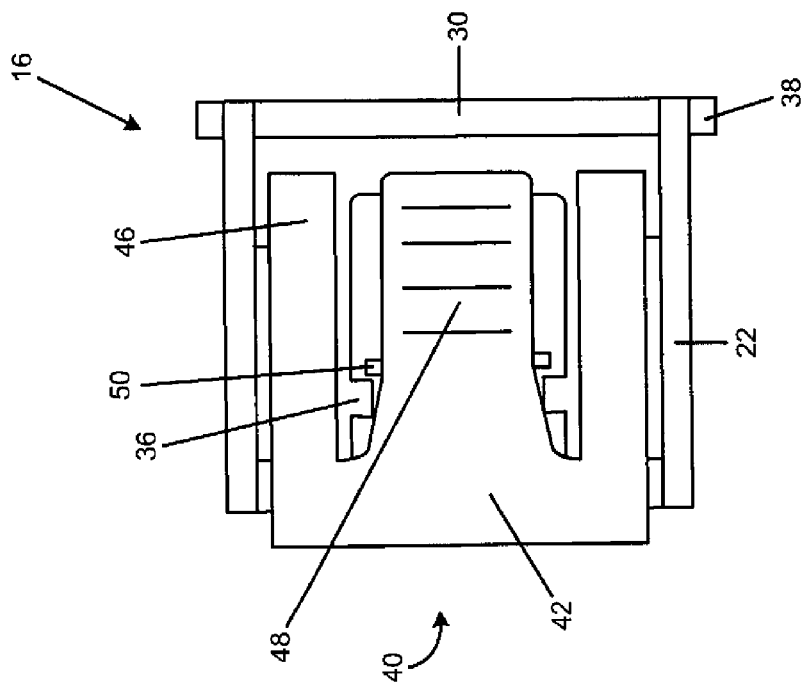
FIG. 5 is an illustration of a top view of the latch mechanism in FIG. 1, in accordance with the first exemplary embodiment of the present disclosure.

FIG. 5 is an illustration of a top view of the latch mechanism 16 in FIG. 1, in accordance with the first exemplary embodiment of the present disclosure. FIG. 6 is an illustration of a side view of the slide part 40 of latch mechanism 16 in FIG. 1, in accordance with the first exemplary embodiment of the present disclosure. The slide part 40 includes at least one slide catch part 50 on one side of the depressible flap 48. The at least one slide catch part 50 is situated to be restrained by the guide catch part 36 of the guide part 20. The slide part 40 also includes a front plate 56, integral with the frame 42 of the slide part 40. At least one lip 54 is integral with the front plate 56. The design of the frame 42, the front plate 56 and the lip 54 may also be constructed in any other method known in the art, including but not limited to a non-integral design, a removable attachment or a permanent attachment.

There are three exemplary situations for engagement of the guide catch part 36 and the slide catch part 50 when the slide part 40 is interconnected with the guide part 20. In other words, the elongated tab 52 would be located within the guiding rail 26 of the guide part 20 in these exemplary situations. The first exemplary situation is when the slide catch part 50 is positioned between the guide catch part 36 and the front end 28 of the guide part 20. Here, the slide catch part 50 would be restrained from moving towards the front end 28 of the guide part 20 by the frame 24, and also restrained from moving towards the rear end 30 of the frame 24 by the guide catch part.

In the second situation, the slide catch part 50 would be engaged directly with the guide catch part 36, positioned such that the slide catch part 50 is below the guide catch part 36. In this arrangement, the slide catch part 50 would be forcibly secured against the guide catch part 36, thereby restraining movement of the slide part 40 with respect to the guide part 20.

The third exemplary situation is when the slide catch part 50 is positioned between the guide catch part 36 and the rear end 30. In this arrangement, the slide catch part 50 is snuggly engaged to the rear side of the guide catch part 36, thereby restraining movement of the slide part 40 in the direction towards the front end 28 of the guide part 20. The slide part 40 may also be restrained from movement towards the rear end 30 of the guide part 20 by a front plate 56 of the slide part 40. The front plate 56 is integral with the slide part 40 and positioned perpendicular to the slide rails 46 and the depressible tab 48. Restraint of the slide part 40 in a rear direction in this third example is created by the interaction of the rear end 28 of the guide part 20 and the front plate 56 of the slide part. This example can be best seen in FIG. 5.

To move the slide part 40 between the arrangements of the first, second or third exemplary situations, the depressible flap 48 is actuated towards or away from the guide catch tab 36 in concert with movement of the slide part 40 in a front or back direction. This action will subsequently move the at least one lip 54, integral with the front plate 56, located parallel to the frame 42 of the slide part 40. The lip 54 is situated to engage the container 10 when the latch mechanism 16 is in the closed position. To facilitate this engagement, the container 10 may include a feature (not shown) to receive the lip 54. In this situation, i.e. the closed position, the lip 54 would engage the feature thereby restraining movement of the portion of the container 10.

Figure 7:
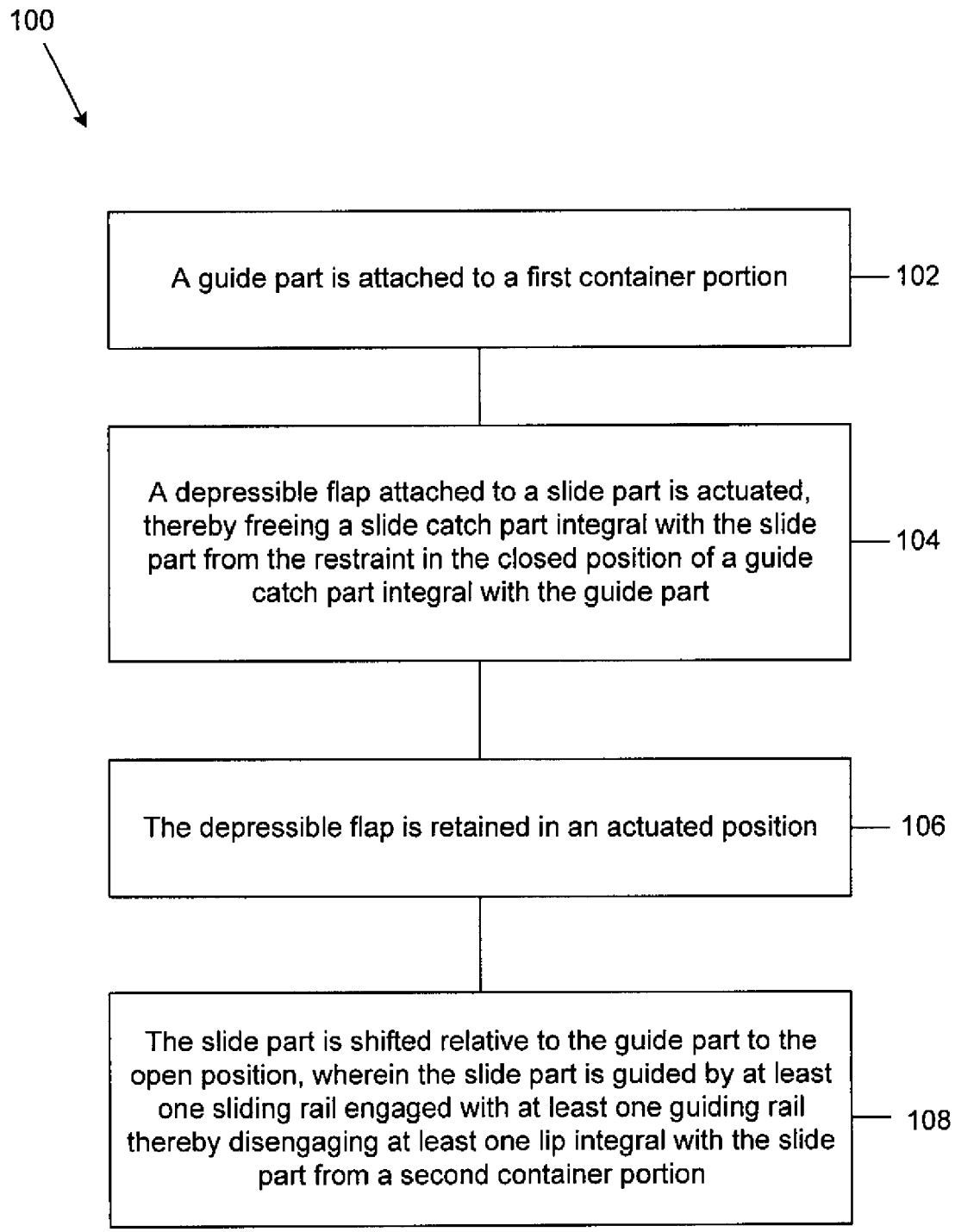
FIG. 7 is a flowchart illustrating a method of unlatching the latch mechanism shown in FIG. 1, in accordance with the first exemplary embodiment of the present disclosure.

FIG. 7 is a flowchart 100 illustrating a method of unlatching the latch mechanism 16 shown in FIG. 1, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a guide part 20 is attached to a first container portion. A depressible flap 48 attached to a slide part 40 is actuated, thereby freeing a slide catch part 50 integral with the slide part 40 from the restraint in the closed position of a guide catch part 36 integral with the guide part 20 (block 104). The depressible flap 48 is retained in an actuated position (block 106). The slide part 40 is shifted relative to the guide part 20 to the open position, wherein the slide part 40 is guided by at least one sliding rail 52 engaged with at least one guiding rail 26 thereby disengaging at least one lip 54 integral with the slide part 40 from a second container portion (block 108).

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

The invention claimed is:

1. A latch mechanism for a container having a first container portion and a second container portion, the latch mechanism comprising:
   a guide part attached to said first container portion;
   a slide part carried by said guide part, shiftable relative to the guide part between a closed position restraining said second container portion and an open position releasing said slide part from said second container portion;
   a guide catch part integral with said guide part;
   said slide part including a depressible flap; and
   a slide catch part positioned on and extending from said depressible flap, wherein interaction between said guide catch part and said slide catch part restrains said slide part against movement from said closed position into said open position, whereby actuating said depressible flap into an actuated positioned releases said slide catch part from being restrained by said guide catch part and frees the slide part to move from said closed position to said open position.

2. The latch mechanism of claim 1, wherein the guide part is secured to said first container portion with a hinge.

3. The latch mechanism of claim 1, wherein the guide part is secured to said first container portion with at least one threaded fastener.

4. The latch mechanism of claim 1, wherein the first container portion is selected from the group consisting of a base of a container; a sidewall of a container; and a lid of a container.

5. The latch mechanism of claim 1, wherein the second container portion is selected from the group consisting of a base of a container; a sidewall of a container; and a lid of a container.

6. The latch mechanism of claim 1, further comprising a guiding rail and a sliding rail, said guiding rail integral with said guide part and said sliding rail integral with said slide part, wherein said guiding rail restrains said sliding rail second retention part in said open position, thereby restraining said slide part from complete separation from said guide part.

7. The latch mechanism of claim 6, wherein said guiding rail is removably attached to said guide part.

8. The latch mechanism of claim 6, wherein said sliding rail is removably attached to said slide part.

9. The latch mechanism of claim 1, further comprising a lip integral with said slide part, wherein the lip engages said second container portion when the slide part is in the closed position.

10. A container comprising:
    a first wall;
    a second wall; and
    a latch mechanism secured to said first wall,
    said latch mechanism having a guide part secured to said first wall and a slide part carried by said guide part, shiftable relative to the guide part between a closed position restraining said second wall to secure said first wall and said second wall, and an open position releasing said slide part from said second wall thereby freeing said first wall from said second wall,
    said guide part including a guide catch part,
    said slide part including a depressible flap and a slide catch part positioned on and extending from said depressible flap,
    said guide catch part positioned to impede said slide catch part thereby restraining said slide part against movement from said closed position into said open position, whereby actuating said depressible flap into an actuated position releases said slide catch part from being restrained by said guide catch part and frees said slide part for movement from said closed position to said open position,
    said guide part having a guiding rail integral with said guide part and said slide part having a sliding rail integral with said slide part, wherein, in said open position, said guiding rail restrains said sliding rail, thereby restraining said slide part from complete separation from said guide part.

11. The container of claim 10, wherein the guide part is secured to said first wall with a hinge.

12. The container of claim 10, wherein the guide part is secured to said first wall with at least one threaded fastener.

13. The container of claim 10, wherein the first wall is selected from the group consisting of: a base of the container; a sidewall of the container; and a lid of the container.

14. The container of claim 10, wherein the second wall is selected from the group consisting of: a base of the container; a sidewall of the container; and a lid of the container.

15. The container of claim 10, further comprising a lip integral with said slide part, wherein the lip engages said second wall when the slide part is in the closed position.

16. A method for unlatching a latch mechanism having an open and a closed position, the method comprising the steps of:
   attaching a guide part to a first container portion;
   actuating a depressible flap attached to a slide part into an actuated position, thereby freeing a slide catch part positioned on and extending from said depressible flap from the restraint in the closed position of a guide catch part integral with said guide part;
   retaining said depressible flap in an actuated position; and
   shifting said slide part relative to said guide part to the open position, wherein said slide part is guided by at least one sliding rail engaged with at least one guiding rail thereby disengaging at least one lip integral with said slide part from a second container portion.

17. The method for unlatching the latch mechanism of claim 16, further comprising the steps of:
   shifting said slide part relative to said guide part to the closed position, wherein said slide part is guided by at least one sliding rail engaged with at least one guiding rail thereby engaging at least one lip integral with said slide part from a second container portion; and
   releasing said depressible flap to restrain the slide catch part with the guide catch part thereby restraining said latch mechanism in the closed position.

18. The method for unlatching the latch mechanism of claim 16, wherein the at least one retaining tab is removably attached to said slide part.

19. The method for unlatching the latch mechanism of claim 16, wherein the slide catch part is removably attached to said slide part.

20. The method for unlatching the latch mechanism of claim 16, wherein the step of attaching a guide part to the first container portion creates a removable attachment.

* * * * *